(12) United States Patent
Rodgers et al.

(10) Patent No.: US 9,623,084 B2
(45) Date of Patent: Apr. 18, 2017

(54) METHODS FOR TREATING MULTIPLE SCLEROSIS

(71) Applicant: UNIVERSITY OF SOUTHERN CALIFORNIA, Los Angeles, CA (US)

(72) Inventors: Kathleen E. Rodgers, Long Beach, CA (US); Gere S. DiZerega, San Luis Obispo, CA (US); Brett Lund, Glendale, CA (US); Eve Kelland, Sun Valley, CA (US); Stan Louie, Los Angeles, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 14/769,363

(22) PCT Filed: Mar. 13, 2014

(86) PCT No.: PCT/US2014/025506
§ 371 (c)(1),
(2) Date: Aug. 20, 2015

(87) PCT Pub. No.: WO2014/151338
PCT Pub. Date: Sep. 25, 2014

(65) Prior Publication Data
US 2016/0000880 A1    Jan. 7, 2016

Related U.S. Application Data

(60) Provisional application No. 61/798,934, filed on Mar. 15, 2013.

(51) Int. Cl.
*A61K 38/22* (2006.01)
*A61K 38/08* (2006.01)

(52) U.S. Cl.
CPC .............. *A61K 38/22* (2013.01); *A61K 38/08* (2013.01)

(58) Field of Classification Search
None
See application file for complete search history.

(56) References Cited

U.S. PATENT DOCUMENTS

| | | |
|---|---|---|
| 5,834,432 A | 11/1998 | diZerega et al. |
| 5,955,430 A | 9/1999 | diZerega et al. |
| 6,096,709 A | 8/2000 | diZerega et al. |
| 6,110,895 A | 8/2000 | diZerega et al. |
| 6,165,978 A | 12/2000 | diZerega et al. |
| 6,177,407 B1 | 1/2001 | diZerega et al. |
| 6,239,109 B1 | 5/2001 | diZerega et al. |
| 6,248,587 B1 | 6/2001 | Rodgers et al. |
| 6,258,778 B1 | 7/2001 | diZerega et al. |
| 6,335,195 B1 | 1/2002 | Rodgers et al. |
| 6,444,646 B1 | 9/2002 | Rodgers et al. |
| 6,455,500 B1 | 9/2002 | diZerega et al. |
| 6,455,501 B1 | 9/2002 | Rodgers et al. |
| 6,475,988 B1 | 11/2002 | Rodgers et al. |
| 6,482,800 B1 | 11/2002 | Rodgers et al. |
| 6,498,138 B1 | 12/2002 | Rodgers et al. |
| 6,730,775 B1 | 5/2004 | diZerega et al. |
| 6,747,008 B1 | 6/2004 | diZerega et al. |
| 6,762,167 B1 | 7/2004 | Rodgers et al. |
| 6,821,953 B1 | 11/2004 | diZerega et al. |
| 6,916,783 B2 | 7/2005 | Rodgers et al. |
| 7,022,675 B2 | 4/2006 | diZerega et al. |
| 7,118,748 B1 | 10/2006 | Rodgers et al. |
| 7,122,523 B2 | 10/2006 | Rodgers et al. |
| 7,173,011 B2 | 2/2007 | Rodgers et al. |
| 7,176,183 B2 | 2/2007 | diZerega et al. |
| 7,288,522 B1 | 10/2007 | diZerega et al. |
| 7,338,938 B2 | 3/2008 | Rodgers et al. |
| 7,744,927 B2 | 6/2010 | Rodgers et al. |
| 7,745,411 B2 | 6/2010 | diZerega et al. |
| 7,776,828 B2 | 8/2010 | diZerega et al. |
| 7,786,085 B2 | 8/2010 | diZerega et al. |
| 8,207,233 B1 | 6/2012 | Rodgers et al. |
| 8,207,234 B1 | 6/2012 | Rodgers et al. |
| 8,536,231 B2 | 9/2013 | Rodgers et al. |
| 9,272,013 B2 | 3/2016 | Rodgers et al. |
| 2002/0147129 A1 | 10/2002 | Mendelsohn et al. |
| 2003/0130196 A1 | 7/2003 | Roders et al. |
| 2010/0055146 A1 | 3/2010 | Haas et al. |
| 2010/0197604 A1 | 8/2010 | Bevec et al. |
| 2014/0205631 A1 | 7/2014 | Larsen et al. |
| 2015/0147283 A1 | 5/2015 | Rodgers et al. |
| 2016/0016946 A1 | 1/2016 | Petasis et al. |
| 2016/0051622 A1 | 2/2016 | Rodgers et al. |

FOREIGN PATENT DOCUMENTS

| WO | 99/42123 A1 | 8/1999 |
|---|---|---|
| WO | 2011/120032 A1 | 9/2011 |

OTHER PUBLICATIONS

't Hart et al., Modelling of multiple sclerosis: lessons learned in a non-human primate, Oct. 2004, The Lancet Neurology 3(10):588-597.*
Werkerle et al., Animal models of multiple sclerosis, 2006, Drug Discovery Today: Disease Models 3(4):359-367.*
Ransohoff, R. M., Animal models of multiple sclerosis: the good, the bad and the bottom line, Aug. 2012, Nature Neuroscience15(8):1074-1077.*
Behan et al., The sad plight of multiple sclerosis research (low on fact, high on fiction): critical data to support it being a neurocristopathy, 2010, Inflammopharmacology 18:265-290.*
International Search Report for PCT/US2014/025506, mailed Jun. 17, 2014.
Laflamme, et al., "Angiotensin Ii induction of neurite outgrowth by AT2 receptors in NG108-15 cells," Journal of Biological Chemistry, 271(37): 22729-22735, Sep. 1996.

(Continued)

*Primary Examiner* — John Ulm
(74) *Attorney, Agent, or Firm* — McDonnell Boehnen Hulbert & Berghoff LLP

(57) ABSTRACT

The present invention provides methods for treating or limiting development of multiple sclerosis by administering angiotensin peptides to a subject with multiple sclerosis or at risk of developing multiple sclerosis.

9 Claims, 4 Drawing Sheets

(56) References Cited

OTHER PUBLICATIONS

Albiston, et al., "Identification and development of specific inhibitors for insulin-regulated aminopeptidase as a new class of cognitive enhancers," British Journal of Pharmacology, 164(1): 37-47, Sep. 2011.

Grammatopoulos, et al., " Angiotensin II protects against alpha-synuclein toxicity and reduces protein aggregation in vitro," Biochemical and Biophysical Research Communication, 363(3): 846-851, Oct. 2007.

* cited by examiner

Chronic Progressive Model

Relapsing-Remitting Model

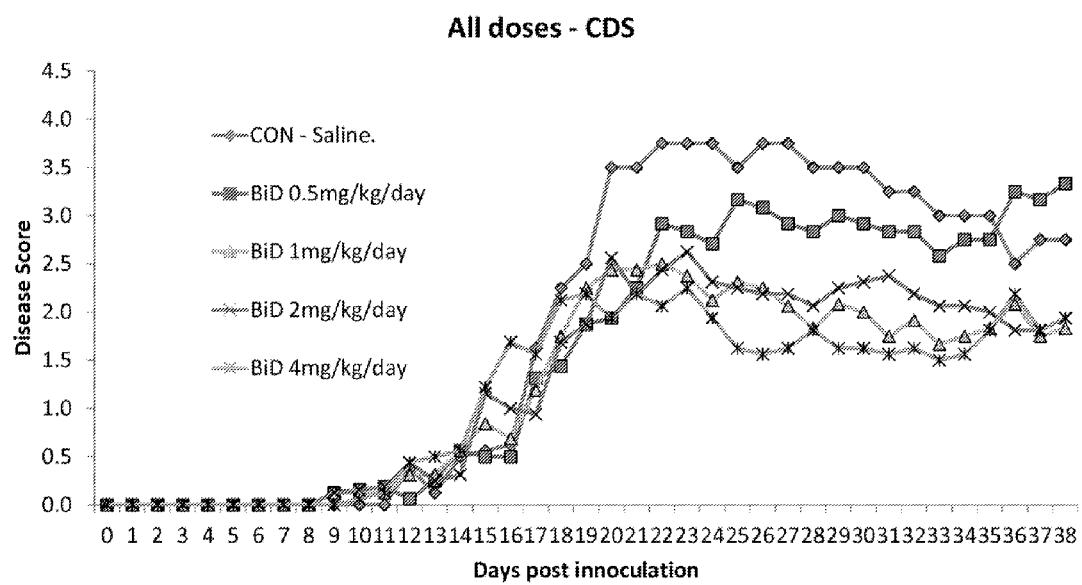
Figure 2 MOG-EAE Model Dose Response BID SC Injection

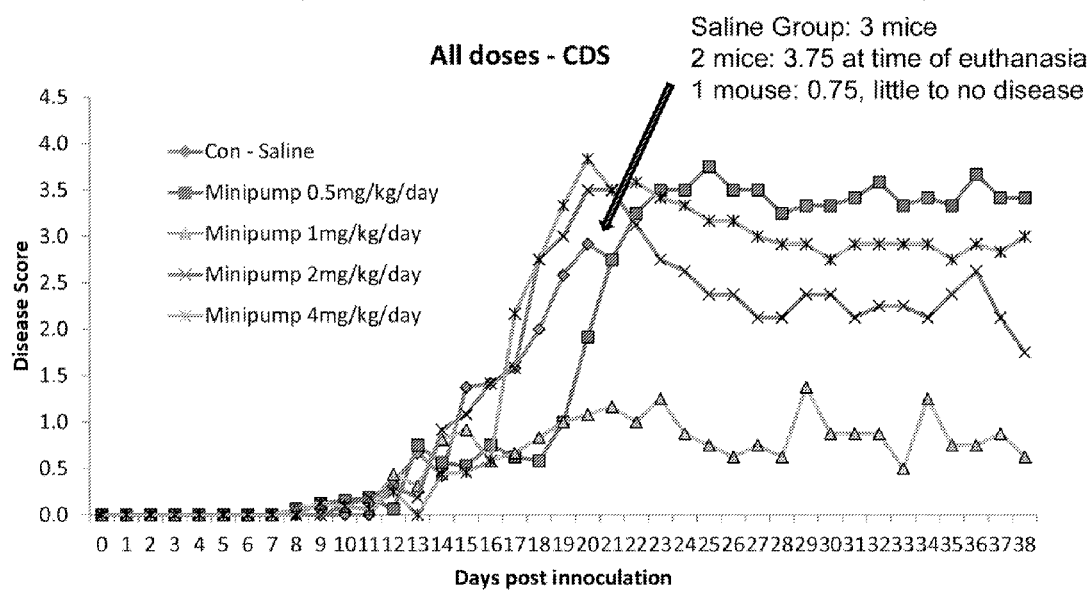

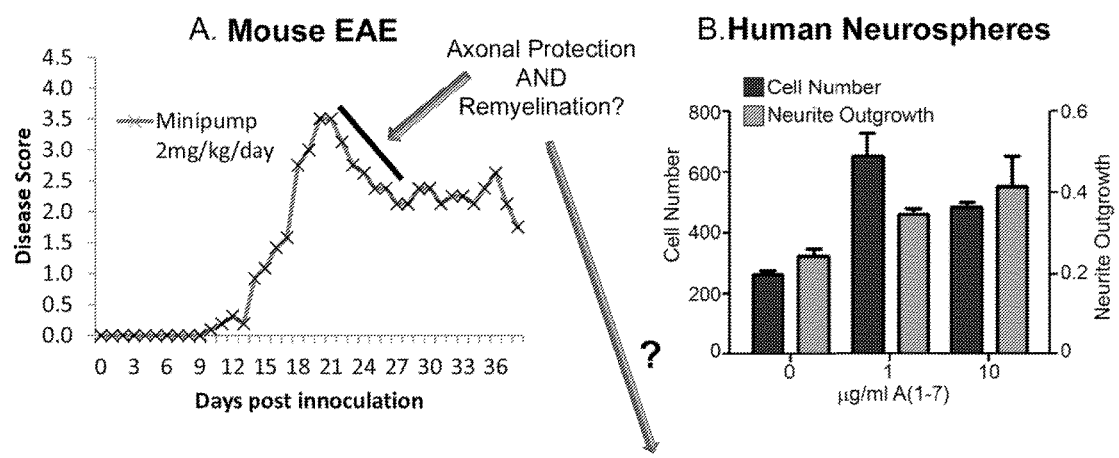
Figure 4 Regeneration by A(1-7)

METHODS FOR TREATING MULTIPLE SCLEROSIS

CROSS-REFERENCE

This application is a U.S. national phase of International Application No. PCT/US2014/025506 filed Mar. 13, 2014, which claims priority to U.S. Provisional Application No. 61/798,934, filed Mar. 15, 2013, the disclosures of which are hereby incorporated by reference in their entireties.

BACKGROUND

Multiple Sclerosis (MS) is a chronic autoimmune and neurodegenerative disease of the central nervous system (CNS) that is characterized by focal infiltration of leukocytes, including myelin-specific T cells, into the CNS, resulting in the destruction of myelin, demyelination, oxidative stress, axonal loss and ultimately, clinical symptoms and neurological disability. Experimental autoimmune encephalomyelitis (EAE) is a well-established animal model of MS that mimics many of the features of MS.

Current treatment options for MS involve the use of immunomodulatory or immune-ablatory agents to slow the disease, but these treatments do not work as effectively in the most severe forms of the disease (e.g. primary-progressive, secondary-progressive MS). Currently there are no FDA approved therapies for the treatment of MS that might also aid in the healing of damaged tissues (neuro-restoration), or the protection of damaged tissue from further disease activity (neuro-protection).

SUMMARY OF THE INVENTION

In a first aspect, the invention provides methods for treating or limiting development of multiple sclerosis, comprising administering to a subject with multiple sclerosis (MS) or at risk of MS an amount effective of an angiotensin peptide or salt thereof to treat or limit development of MS. In one embodiment, the method is for treating MS. In one embodiment, the subject has a chronic progressive or relapse-remitting course of MS. In a further embodiment, the treating results in one or more clinical outcomes, compared to MS subjects not treated with angiotensin peptide, selected from the group consisting of:

(a) decrease in MS disease progression;
(b) decrease in MS disease severity;
(c) decrease in nerve cell demyelination;
(d) decrease in frequency or severity of relapsing MS attacks;
(e) decrease in MS symptoms;
(f) healing of damaged nerve tissue (neuro-restoration);
(g) increase in remyelination of demyelinated nerves in the central nervous system (neuro-restoration/protection);
(h) protection of damaged nerve tissue from further disease activity (neuro-protection);
(i) promoting neuronal outgrowth (neuro-regeneration) in the central nervous system; and
(j) decrease in disability caused by MS.

In another embodiment, the method is for limiting development of MS. In a further embodiment, the angiotensin peptide or salt thereof comprises a sequence of at least four contiguous amino acids of groups $R^1$-$R^8$ in the sequence of general formula I $$R^1\text{-}R^2\text{-}R^3\text{-}R^4\text{-}R^5\text{-}R^6\text{-}R^7\text{-}R^8 \quad \text{(SEQ ID NO: 1)}$$

wherein $R^1$ is selected from the group consisting of H, Asp, Glu, Asn, Acpc (1-aminocyclopentane carboxylic acid), Ala, $Me^2$Gly, Pro, Bet, Glu(NH$_2$), Gly, Asp(NH$_2$) and Suc, or is absent, $R^2$ is selected from the group consisting of Arg, Lys, Ala, Cit, Orn, Ser(Ac), Sar, D-Arg and D-Lys, $R^3$ is selected from the group consisting of Val, Ala, Leu, norLeu, Ile, Gly, Lys, Pro, Aib, Acpc and Tyr;

$R^4$ is selected from the group consisting of Tyr, Tyr(PO$_3$)$_2$, Thr, Ser, homoSer, azaTyr, and Ala;

$R^5$ is selected from the group consisting of Ile, Ala, Leu, norLeu, Val and Gly;

$R^6$ is selected from the group consisting of His, Arg or 6-NH$_2$-Phe;

$R^7$ is selected from the group consisting of Pro or Ala; and $R^8$ is selected from the group consisting of Phe, Phe(Br), Ile and Tyr, or a salt thereof;

excluding sequences including $R^4$ as a terminal Tyr group.

In another embodiment, the angiotensin peptide or salt thereof comprises or consists of A(1-7), (Asp-Arg-Val-Tyr-Ile-His-Pro (SEQ ID NO: 4), or a salt thereof.

In one embodiment, the angiotensin peptide is administered in a polymer formulation. In a further embodiment, the polymer formulation comprises a Poly-D, L-Lactic-Co-Glycolic Acid (PLGA) polymer, a poly-lactic acid (PLA), and co-polymers thereof, polycaprolactone particles, and chitosan nanoparticles.

DESCRIPTION OF THE FIGURES

FIG. 2 is a graphical representation of dose response data obtained from twice per day subcutaneous injections of the angiotensin peptide in a chronic progressive MS model.

FIG. 3 is a graphical representation of dose response data obtained from continuous delivery of the angiotensin peptide in a chronic progressive MS model.

FIG. 4 is a graphical representation of neuronal regeneration resulting from continuous delivery of the angiotensin peptide in a progressive MS model (A), and axonal outgrowth from in vitro studies using human neurospheres (B).

DETAILED DESCRIPTION OF THE INVENTION

Figure 1:
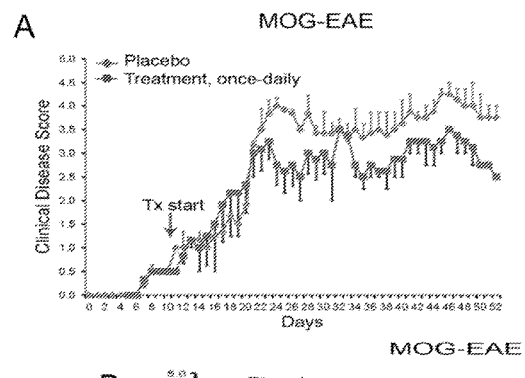
FIG. 1 is a graphical representation of pre-clinical data obtained from once a day subcutaneous injections of the angiotensin peptide in a chronic progressive model (A, B) and a relapsing-remitting model (C) of multiple sclerosis (MS).
Figure 1:
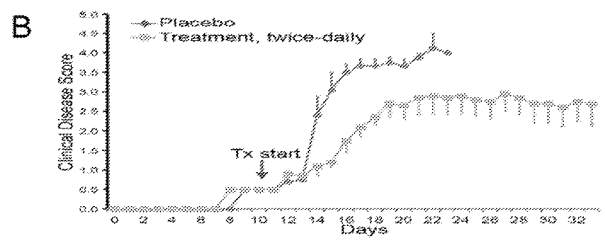
Figure 1:
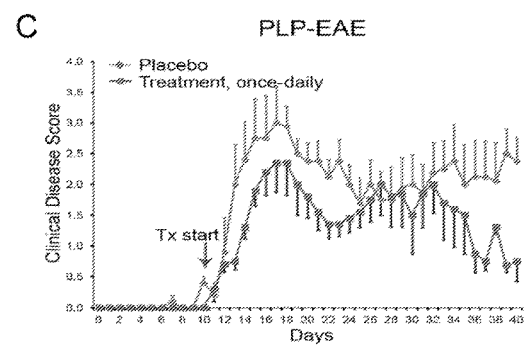

As used herein, the singular forms "a," "an" and "the" include plural referents unless the context clearly dictates otherwise. "And" as used herein is interchangeably used with "or" unless expressly stated otherwise.

All embodiments within and between different aspects of the invention can be combined unless the context clearly dictates otherwise.

As used herein, the term "about" means+/−5% of the relevant measurement or unit.

In a first aspect, the invention provides methods for treating or limiting development of multiple sclerosis, comprising administering to a subject with multiple sclerosis (MS) or at risk of MS an amount effective of an angiotensin peptide or salt thereof to treat or limit development of MS.

The inventors have demonstrated that the methods of the invention delay disease progression and improve disease course in two different animal models of MS, and appear to promote neuronal regeneration/remyelination in an MS animal model.

MS, also known as disseminated sclerosis or encephalomyelitis disseminata, is a chronic autoimmune and neurodegenerative disease of the central nervous system (CNS) that is characterized by focal infiltration of leukocytes, including myelin-specific T cells, into the CNS, resulting destruction of myelin, demyelination, oxidative stress, axonal loss and ultimately, clinical symptoms and neurological disability. People with MS typically experience one of four disease courses, each of which might be mild, moderate, or severe:

(1) Relapsing-Remitting MS: Clearly defined attacks of worsening neurologic function. These attacks ("relapses" or "flare-ups") are followed by partial or complete recovery periods (remissions), during which no disease progression occurs.

(2) Primary-Progressive MS: Slowly worsening neurologic function from the outset, with no distinct relapses or remissions. The rate of progression may vary over time, with occasional plateaus and temporary minor improvements.

(3) Secondary-Progressive MS: Following an initial period of relapsing-remitting MS, a secondary-progressive disease course occurs in which the disease worsens more steadily, with or without occasional flare-ups, minor recoveries (remissions), or plateaus.

(4) Progressive-Relapsing MS: Steadily worsening disease from the beginning, but with clear attacks of worsening neurologic function along the way. There may or may not be some recovery following these relapses, but the disease continues to progress without remissions.

The subject is a human. If the methods are for treating a subject with MS, the subject may be experiencing any of the MS disease courses noted herein (relapse-remitting, primary progressive, secondary-progressive, and progressive-relapsing).

As used herein, "treating" MS means providing any clinical benefit to a subject with MS. The clinical benefit may be temporary or long-lasting. In various non-limiting embodiments, the treatment results in one or more clinical outcome (as compared to subjects not treated with angiotensin peptide) selected from the group consisting of:

(a) decrease in MS disease progression;
(b) decrease in MS disease severity;
(c) decrease in nerve cell demyelination;
(d) decrease in frequency or severity of relapsing MS attacks;
(e) decrease in MS clinical symptoms;
(f) healing of damaged nerve tissue (neuro-restoration);
(g) increase in remyelination of demyelinated nerves in the central nervous system (neuro-restoration/protection);
(h) protection of damaged nerve tissue from further disease activity (neuro-protection);
(i) promoting neuronal outgrowth (neuro-regeneration) in the central nervous system; and
(j) decrease in disability caused by MS.

As used herein, "limiting development" of MS means providing limiting development of symptoms or disease in a subject that is at risk of developing MS. Exemplary subjects at risk of MS include, but are not limited to subjects with a relative (identical twin, non-identical twin, sibling, parent, etc.) that has MS and subjects that have suffered a clinically isolated syndrome (CIS), which is a subject's first neurological episode, caused by inflammation or demyelination of nerve tissue.

Exemplary characteristics of MS include, but are not limited to focal infiltration of leukocytes into the CNS, destruction of myelin, demyelination, oxidative stress, axonal loss, clinical symptoms and neurological disability. Exemplary clinical symptoms include, but are not limited to loss of sensitivity or changes in sensation such as tingling, pins and needles or numbness, muscle weakness of variable severity, very pronounced reflexes, muscle spasms, or difficulty in moving; difficulties with coordination and balance (ataxia); spasticity; problems with speech or swallowing, visual problems (nystagmus, optic neuritis or double vision), fatigue, acute or chronic pain, bladder and bowel difficulties, incontinence, reduced cognitive ability, depression, anxiety and other emotional abnormalities, sexual dysfunction, Uhthoff's phenomenon (a worsening of symptoms due to exposure to higher than usual temperatures), and Lhermitte's sign (an electrical sensation that runs down the back when bending the neck).

These clinical benefits may be demonstrated using any suitable process for measuring clinical benefits, including but not limited to clinical findings of an attending physician, assessing the clinical disease activity, measured by appropriate instrumentation (magnetic resonance imaging (MRI), positron emission tomography (PET), optical coherence tomography (OCT), etc.) in combination with a full neurological assessments of the patient. Those of skill in the art are well versed in how to measure clinical disease activity in MS patients and in how to measure the clinical benefits of treatment in MS patients.

In one embodiment, the angiotensin peptide comprises or consists of A(1-7), with an amino acid sequence of Asp-Arg-Val-Tyr-Ile-His-Pro (SEQ ID NO: 4).

In another embodiment, the peptides for use in the invention comprise or consist of a sequence of at least four contiguous amino acids of groups $R^1$-$R^8$ in the sequence of general formula I $$R^1\text{-}R^2\text{-}R^3\text{-}R^4\text{-}R^5\text{-}R^6\text{-}R^7\text{-}R^8 \quad (\text{SEQ ID NO: 1})$$

wherein $R^1$ is selected from the group consisting of H, Asp, Glu, Asn, Acpc (1-aminocyclopentane carboxylic acid), Ala, $Me^2$Gly, Pro, Bet, Glu($NH_2$), Gly, Asp($NH_2$) and Suc, or is absent, $R^2$ is selected from the group consisting of Arg, Lys, Ala, Cit, Orn, Ser(Ac), Sar, D-Arg and D-Lys, $R^3$ is selected from the group consisting of Val, Ala, Leu, norLeu, Ile, Gly, Lys, Pro, Aib, Acpc and Tyr;

$R^4$ is selected from the group consisting of Tyr, Tyr($PO_3$)$_2$, Thr, Ser, homoSer, azaTyr, and Ala;

$R^5$ is selected from the group consisting of Ile. Ala. Leu, norLeu, Val and Gly;

$R^6$ is selected from the group consisting of His, Arg or 6-$NH_2$-Phe;

$R^7$ is selected from the group consisting of Pro or Ala; and $R^8$ is selected from the group consisting of Phe, Phe(Br), Ile and Tyr, excluding sequences including $R^4$ as a terminal Tyr group.

Exemplary AT2 agonists useful in the practice of the invention include the AII analogues set forth above subject to the restriction that $R^6$ is p-$NH_2$-Phe.

In a further preferred embodiment of each of the above embodiments (SEQ ID NO: 15), $R^1$ is selected from the group consisting of Asp and Glu, or is absent;

$R^2$ is selected from the group consisting of Arg, Lys, and Ala;

$R^3$ is selected from the group consisting of Val, Ala, Leu, norLeu, Ile, Gly, Lys, and Pro;

$R^4$ is selected from the group consisting of Tyr and homoSer;

$R^5$ is selected from the group consisting of Ile. Ala. Len, norLeu, Val and Gly;

$R^6$ is selected from the group consisting of His and Arg;

$R^7$ is selected from the group consisting of Pro or Ala; and $R^8$ is selected from the group consisting of Phe, Ile, or is absent.

In alternate embodiments, the peptides comprise or consist of at least five, six, seven, or eight contiguous amino acids of groups $R^1$-$R^8$ in the sequence of general formula I. In a further alternative, the polypeptides consist essentially of a sequence of at least four, five, six, seven, or eight contiguous amino acids of groups $R^1$-$R^8$ in the sequence of general formula I.

Particularly preferred combinations for $R^1$ and $R^2$ are Asp-Arg, Asp-Lys. Glu-Arg and Glu-Lys. Particularly preferred embodiments of this class include the following: AIII or AII(2-8), Arg-Val-Tyr-Ile-His-Pro-Phe [SEQ ID NO:2]; AII(3-8), also known as des1-AIII or AIV, Val-Tyr-Ile-His-Pro-Phe [SEQ ID NO:3]; AII(1-7), Asp-Arg-Val-Tyr-Ile-His-Pro [SEQ ID NO:4]; AII(2-7). Arg-Val-Tyr-Ile-His-Pro [SEQ ID NO:5]; AII(3-7), Val-Tyr-Ile-His-Pro [SEQ ID NO:6]; AII(5-8). Ile-His-Pro-Phe [SEQ ID NO:7]; AII(1-6). Asp-Arg-Val-Tyr-Ile-His [SEQ ID NO:8]; AII(1-5). Asp-Arg-Val-Tyr-Ile [SEQ ID NO:9]; AII(1-4). Asp-Arg-Val-Tyr [SEQ ID NO: 10]; and AII(1-3), Asp-Arg-Val. Other preferred embodiments include: Arg-norLeu-Tyr-Ile-His-Pro-Phe [SEQ ID NO: 11] and Arg-Val-Tyr-norLeu-His-Pro-Phe [SEQ ID NO:12]. Still another preferred embodiment encompassed within the scope of the invention is a peptide having the sequence Asp-Arg-Pro-Tyr-Ile-His-Pro-Phe [SEQ ID NO:13].

Other preferred embodiments comprise or consist of

| | |
|---|---|
| Asp-Arg-Val-Tyr-Val-His-Pro-Phe | SEQ ID NO: 18 |
| Asn-Arg-Val-Tyr-Val-His-Pro-Phe | SEQ ID NO: 19 |
| Ala-Pro-Gly-Asp-Arg-Ile-Tyr-Val-His-Pro-Phe | SEQ ID NO: 20 |
| Glu-Arg-Val-Tyr-Ile-His-Pro-Phe | SEQ ID NO: 21 |
| Asp-Lys-Val-Tyr-Ile-His-Pro-Phe | SEQ ID NO: 22 |
| Asp-Arg-Ala-Tyr-Ile-His-Pro-Phe | SEQ ID NO: 23 |
| Asp-Arg-Val-Thr-Ile-His-Pro-Phe | SEQ ID NO: 24 |
| Asp-Arg-Val-Tyr-Leu-His-Pro-Phe | SEQ ID NO: 25 |
| Asp-Arg-Val-Tyr-Ile-Arg-Pro-Phe | SEQ ID NO: 26 |
| Asp-Arg-Val-Tyr-Ile-His-Ala-Phe | SEQ ID NO: 27 |
| Asp-Arg-Val-Tyr-Ile-His-Pro-Tyr | SEQ ID NO: 28 |
| Pro-Arg-Val-Tyr-Ile-His-Pro-Phe | SEQ ID NO: 29 |
| Asp-Arg-Pro-Tyr-Ile-His-Pro-Phe | SEQ ID NO: 13 |
| Asp-Arg-Val-Tyr(PO$_3$)$_2$-Ile-His-Pro-Phe | SEQ ID NO: 30 |
| Asp-Arg-norLeu-Tyr-Ile-His-Pro-Phe | SEQ ID NO: 31 |
| Asp-Arg-Val-Tyr-norLeu-His-Pro-Phe | SEQ ID NO: 32 |
| Asp-Arg-Val-homoSer-Tyr-Ile-His-Pro-Phe | SEQ ID NO: 33 |

Another class of peptides of particular interest in accordance with the present invention are those of the general formula II:

$$R^2\text{-}R^3\text{-}R^4\text{-}R^5\text{-}R^6\text{-}R^7\text{-}R^8 \quad \text{(SEQ ID NO: 34)}$$

in which $R^2$ is selected from the group consisting of H, Arg, Lys, Ala, Orn, Citron, Ser(Ac), Sar, D-Arg and D-Lys;

$R^3$-$R^8$ are as defined above, and excluding sequences including $R^4$ as a terminal Tyr group.

A particularly preferred subclass of the compounds of general formula II has the formula:

$$R^2\text{-}R^3\text{-Tyr-}R^5\text{-His-Pro-Phe} \quad \text{[SEQ ID NO: 35]}$$

wherein $R^2$, $R^3$ and $R^5$ are as previously defined. Particularly preferred is angiotensin III of the formula Arg-Val-Tyr-Ile-His-Pro-Phe [SEQ ID NO:2]. Other preferred compounds include peptides having the structures Arg-Val-Tyr-Gly-His-Pro-Phe [SEQ ID NO:36] and Arg-Val-Tyr-Ala-His-Pro-Phe [SEQ ID NO:37].

In the above formulas, the standard three-letter abbreviations for amino acid residues are employed. Other residues are abbreviated as follows:

TABLE 1

| Abbreviation for Amino Acids | |
|---|---|
| Me$^2$Gly | N,N-dimethylglycyl |
| Bet | 1-carboxy-N,N,N-trimethylmethanaminium hydroxide inner salt (betaine) |
| Suc | Succinyl |
| Phe(Br) | p-bromo-L-phenylalanyl |
| azaTyr | aza-α'-homo-L-tyrosyl |
| Acpc | 1-aminocyclopentane carboxylic acid |
| Aib | 2-aminoisobutyric acid |
| Sar | N-methylglycyl (sarcosine) |
| Cit | Citron |
| Orn | Ornithine |
| NorLeu (Nle) | NorLeucine |
| HomoSer | HomoSerine (isotheronine) |

It has been suggested that AII and its analogues adopt either a gamma or a beta turn (Regoli, et al., *Pharmacological Reviews* 26:69 (1974)). In general, it is believed that neutral side chains in position $R^3$, $R^5$ and $R^7$ may be involved in maintaining the appropriate distance between active groups in positions $R^4$, $R^6$ and $R^8$ primarily responsible for binding to receptors and/or intrinsic activity. Hydrophobic side chains in positions $R^3$, $R^5$ and $R^8$ may also play an important role in the whole conformation of the peptide and/or contribute to the formation of a hypothetical hydrophobic pocket.

Appropriate side chains on the amino acid in position $R^2$ may contribute to affinity of the compounds for target receptors and/or play an important role in the conformation of the peptide. For this reason. Arg and Lys are particularly preferred as $R^2$. Alternatively, $R_2$ may be H, Ala, Orn, Citron, Ser(Ac), Sar, D-Arg, or D-Lys.

For purposes of the present invention, it is believed that $R^3$ may be involved in the formation of linear or nonlinear hydrogen bonds with $R^5$ (in the gamma turn model) or $R^6$ (in the beta turn model). $R^3$ would also participate in the first turn in a beta antiparallel structure (which has also been proposed as a possible structure). In contrast to other positions in general formula I, it appears that beta and gamma branching are equally effective in this position. Moreover, a single hydrogen bond may be sufficient to maintain a relatively stable conformation. Accordingly, $R^3$ may suitably be selected from Lys, Val, Ala, Leu, norLeu, Ile, Gly, Pro, Aib, Acpc and Tyr.

With respect to $R^4$, conformational analyses have suggested that the side chain in this position (as well as in $R^3$ and $R^5$) contribute to a hydrophobic cluster believed to be essential for occupation and stimulation of receptors. Thus, $R^4$ is preferably selected from Tyr, Thr, Tyr $(PO_3)_2$, homoSer, Ser and azaTyr. In this position, Tyr is particularly preferred as it may form a hydrogen bond with the receptor site capable of accepting a hydrogen from the phenolic hydroxyl (Regoli, et al. (1974), supra). It has also been found that $R^4$ can be Ala, and that it can be used for cyclization of angiotension peptides.

In position $R^5$, an amino acid with a β aliphatic or alicyclic chain is particularly desirable. Therefore, while Gly is suitable in position $R^5$, it is preferred that the amino acid in this position be selected from Ile, Ala, Len, norLeu, and Val.

In another embodiment, in peptides of particular interest in accordance with the present invention $R^6$ is His, Arg or 6-$NH_2$-Phe. The unique properties of the imidazole ring of histidine (e.g., ionization at physiological pH, ability to act as proton donor or acceptor, aromatic character) are believed to contribute to its particular utility as $R^6$. For example, conformational models suggest that His may participate in hydrogen bond formation (in the beta model) or in the second turn of the antiparallel structure by influencing the orientation of $R^7$. Similarly, it is presently considered that $R^7$ should be Pro or Ala in order to provide the most desirable orientation of $R^8$. In position $R^8$, both a hydrophobic ring and an anionic carboxyl terminal appear to be particularly useful in binding of the analogues of interest to receptors; therefore, Tyr, Ile, Phe(Br), and especially Phe are preferred for purposes of the present invention.

Analogues of particular interest include the following:

TABLE 2

Angiotensin H Analogues

| AII Analogue Name | Amino Acid Sequence | Sequence Identifier |
|---|---|---|
| Analogue 1 | Asp-Arg-Val-Tyr-Val-His-Pro-Phe | SEQ ID NO: 18 |
| Analogue 2 | Asn-Arg-Val-Tyr-Val-His-Pro-Phe | SEQ ID NO: 19 |
| Analogue 3 | Ala-Pro-Gly-Asp-Arg-Ile-Tyr-Val-His-Pro-Phe | SEQ ID NO: 20 |
| Analogue 4 | Glu-Arg-Val-Tyr-Ile-His-Pro-Phe | SEQ ID NO: 21 |
| Analogue 5 | Asp-Lys-Val-Tyr-Ile-His-Pro-Phe | SEQ ID NO: 22 |
| Analogue 6 | Asp-Arg-Ala-Tyr-Ile-His-Pro-Phe | SEQ ID NO: 23 |
| Analogue 7 | Asp-Arg-Val-Thr-Ile-His-Pro-Phe | SEQ ID NO: 24 |
| Analogue 8 | Asp-Arg-Val-Tyr-Leu-His-Pro-Phe | SEQ ID NO: 25 |
| Analogue 9 | Asp-Arg-Val-Tyr-Ile-Arg-Pro-Phe | SEQ ID NO: 26 |
| Analogue 10 | Asp-Arg-Val-Tyr-Ile-His-Ala-Phe | SEQ ID NO: 27 |
| Analogue 11 | Asp-Arg-Val-Tyr-Ile-His-Pro-Tyr | SEQ ID NO: 28 |
| Analogue 12 | Pro-Arg-Val-Tyr-Ile-His-Pro-Phe | SEQ ID NO: 29 |
| Analogue 13 | Asp-Arg-Pro-Tyr-Ile-His-Pro-Phe | SEQ ID NO: 13 |
| Analogue 14 | Asp-Arg-Val-Tyr(P03)2-Ile-His-Pro-Phe | SEQ ID NO: 30 |
| Analogue 15 | Asp-Arg-norLeu-Tyr-Ile-His-Pro-Phe | SEQ ID NO: 31 |
| Analogue 16 | Asp-Arg-Val-Tyr-norLeu-His-Pro-Phe | SEQ ID NO: 32 |
| Analogue 17 | Asp-Arg-Val-homoSer-Tyr-Ile-His-Pro-Phe | SEQ ID NO: 33 |

Other particularly preferred embodiments include:

| | | | |
|---|---|---|---|
| 1GD | Ala4-AII(1-7) | DRVAIHP | SEQ ID NO: 38 |
| 2GD | Pro3-AII(1-7) | DRPYIHP | SEQ ID NO: 39 |
| 5GD | Lys3-AII(1-7) | DRKYIHP | SEQ ID NO: 40 |
| 9GD | NorLeu-AII(1-7) | DR(nor)YIHP | SEQ ID NO: 41 |
| GSD 28 | Ile8-AII | DRVYIHPI | SEQ ID NO: 42 |
| | Ala3aminoPhe6 AII: | RVAIHPF | SEQ ID NO: 43 |
| | Ala3-AIII | RVAIHPF | SEQ ID NO: 44 |
| | Gly1-AII | GRVYIHPF | SEQ ID NO: 45 |
| | NorLeu4-AIII | --RVYnLHPF | SEQ ID NO: 46 |
| | Acpc3-AII | DR(Acpc)YIHPF | SEQ ID NO: 47 |

-continued

| | | | |
|---|---|---|---|
| GSD 37B | Orn²-AII | D(Orn)VYIHPF | SEQ ID NO: 48 |
| GSD38B | Citron²-AII | D(Citron)VYIHPF | SEQ ID NO: 49 |
| 3GD | Pro³Ala⁴-AII(1-7) | DRPAIHP | SEQ ID NO: 50 |
| 8GD | Hydroxy-Pro³-AII (1-7) | DRP(OH)AIHP | SEQ ID NO: 51 |

In another embodiment, the peptides may include any of those disclosed in published US patent application US20100055146, which is incorporated by reference herein in its entirety. In various embodiments, the polypeptide is:

a 4,7-cyclized analog of Angiotensin II (Ang(1-8), or any of its analogues disclosed herein;

a 4,7-cyclized analog of Angiotensin III (Ang(2-8)), or any of its analogues disclosed herein;

a 4,7-cyclized analog of Angiotensin IV (Ang(3-8)), or any of its analogues disclosed herein; or a 4,7-cyclized analog of Ang(1-7), or any of its analogues disclosed herein.

In another embodiment, the methods comprise administering an agonist of the MAS receptor. Any suitable polypeptide or non-polypeptide agonist of the MAS receptor may be used, including but not limited to A(1-7) and analogues thereof. A779 (D-Ala A(1-7); available from Sigma Chemical Co.) and AVE0991, (see, for example. Pinheiro et al., Hypertension. 2004 October; 44(4):490-6. Epub 2004 Aug. 23).

The polypeptides for use in the present invention may be linear or cyclized in any suitable manner, such as those described in WO2008/018792, including but not limited to polypeptides comprising a thioether bridge between positions 4 and 7, or other positions.

The polypeptides may be recombinantly expressed or chemically synthesized using any suitable techniques, which are well within the level of those of skill in the art.

Suitable acids which are capable of forming salts with peptide (such as A(1-7)) include inorganic acids such as hydrochloric acid, hydrobromic acid, perchloric acid, nitric acid, thiocyanic acid, sulfuric acid, phosphoric acid and the like; and organic acids such as formic acid, acetic acid, propionic acid, glycolic acid, lactic acid, pyruvic acid, oxalic acid, malonic acid, succinic acid, maleic acid, fumaric acid anthranilic acid, cinnamic acid, naphthalene sulfonic acid, sulfanilic acid and the like. Suitable bases capable of forming salts with peptide (such as A(1-7)) include inorganic bases such as sodium hydroxide, ammonium hydroxide, potassium hydroxide and the like; and organic bases such as mono-, di- and tri-alkyl and aryl amines (e.g., triethylamine, diisopropyl amine, methyl amine, dimethyl amine and the like) and optionally substituted ethanol-amines (e.g., ethanolamine, diethanolamine and the like).

Pharmaceutical compositions for use in the methods of the invention may be made up in a solid form (including granules, powders or suppositories), in aerosolized form, or in a liquid form (e.g., solutions, suspensions, or emulsions). The pharmaceutical compositions may be applied in a variety of solutions. Suitable solutions for use in accordance with the invention are sterile, dissolve sufficient amounts of the peptide (such as A(1-7)), and are not harmful for the proposed application. In this regard, the compounds of the present invention are very stable but are hydrolyzed by strong acids and bases. The compounds of the present invention are soluble in organic solvents and in aqueous solutions at pH 5-8. The pharmaceutical compositions may be subjected to conventional pharmaceutical operations such as sterilization and/or may contain conventional adjuvants.

In other embodiments of all aspects of the invention, the pharmaceutical compositions of the present invention may further comprise one or more other therapeutics as needed by a given subject.

The angiotensin peptide (such as A(1-7)) or salts thereof can further be derivatized to provide enhanced half-life, for example, by linking to polyethylene glycol or lipidized to increase oral bioavailability and/or prolong plasma half-life. The peptide (such as A(1-7)) or salts thereof may comprise L-amino acids, D-amino acids (which are resistant to L-amino acid-specific proteases in vivo), a combination of D- and L-amino acids, and various "designer" amino acids (e.g., β-methyl amino acids, Cα-methyl amino acids, and Nα-methyl amino acids, etc.) to convey special properties. In other embodiments, the N-terminus may be acetylated and/or the C-terminus may be amidated.

In addition, the angiotensin peptide (such as A(1-7)) or salts thereof can have peptidomimetic bonds. For example, an A(1-7) peptide may be generated that incorporates a reduced peptide bond, i.e., $R_1$—$CH_2$—$NH$—$R_2$, where $R_1$ and $R_2$ are amino acid residues or sequences. A reduced peptide bond may be introduced as a dipeptide subunit. Such polypeptides are resistant to protease activity, and possess an extended half-live in vivo.

Any suitable amount effective of the angiotensin peptide (such as A(1-7)) may be used in the methods of the invention, as appropriate for a given use and as determined by an attending physician. In various non-limiting embodiments, the polypeptide is administered in a dosage of 10 μg/kg/day, 50 μg/day μg/kg/day, 100 μg/kg/day, 250 μg/kg/day, 500 μg/kg/day, 1000 μg/kg/day, 2000 μg/kg/day, 3000 μg/kg/day, 4000 μg/kg/day or more. In various embodiments, the amount of peptide (such as A(1-7)) or pharmaceutical salt thereof is sufficient to provide a dosage to a patient of between 0.01 μg/kg and 10 mg/kg; 0.1 μg/kg and 5 mg/kg; 0.1 μg/kg and 1000 μg/kg; 0.1 μg/kg and 900 μg/kg; 0.1 μg/kg and 900 μg/kg 0.1 μg/kg and 800 μg/kg; 0.1 μg/kg and 700 μg/kg; 0.1 μg/kg and 600 μg/kg; 0.1 μg/kg and 500 μg/kg; or 0.1 μg/kg and 400 μg/kg. Polypeptide can be administered as often as appropriate to achieve the desired result, including but not limited once per day, twice per day, every other day, three times per week, twice per week, once per week, or via any continuous delivery method deemed suitable.

The angiotensin peptide (such as A(1-7)) or salts or ester analogs of the peptides thereof can be administered by any suitable route, including but not limited to inhalation, dermal, subcutaneous, intradermal, transdermal (for example, by slow-release polymers), intramuscular, intraperitoneal, intravenous, oral, aural, epidural, anal or vaginal (for example, by suppositories), pulmonary route, intratracheal instillation (pumps or delivery vehicles), intranasal routes, infusion or bolus injection, needle patch delivery, or absorption through epithelial or mucocutaneous linings (sublingual, buccal, etc.)

For administration, the angiotensin peptides, salts thereof, or pharmaceutical compositions thereof are ordinarily combined with one or more adjuvants appropriate for the indicated route of administration. The compounds may be admixed with lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinylpyrrolidine, and/or polyvinyl alcohol, and tableted or encapsulated for conventional administration. Alternatively, the compositions of this invention may be dissolved in saline, water, polyethylene glycol, propylene glycol, carboxymethyl cellulose colloidal solutions, hydroxyethyl cellulose colloidal solutions, ethanol, corn oil, peanut oil, cottonseed oil, sesame oil, tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art. Methods for the production of these formulations with the peptides or pharmaceutical compositions of the present invention are apparent to those of ordinary skill in the art.

In some embodiments, the pharmaceutical compositions are formulated as a gel. In these embodiments, the angiotensin peptide, or salt thereof, may be present in the composition at a concentration of about 0.001% to about 3% on a weight (mg)/volume (ml) basis, or on a weight/weight (mg) basis. In various further embodiments, the polypeptide, or salt thereof, is administered in a pharmaceutical formulation at a concentration of about 0.005% to about 3%; about 0.01% to about 3%; about 0.05% to about 3%; about 0.01% to about 3%; about 0.5% to about 3%; about 1% to about 3%; about 2% to about 3%; about 0.005% to about 2%; about 0.01% to about 2%; about 0.05% to about 2%; about 0.01% to about 2%; about 0.5% to about 2%; about 1% to about 2%; about 0.005% to about 1%; about 0.01% to about 1%; about 0.05% to about 1%; about 0.01% to about 1%; about 0.5% to about 1%; about 0.005% to about 0.75%; about 0.01% to about 0.75%; about 0.005% to about 0.75%; about 0.01% to about 0.75%; about 0.03% to about 1%; about 0.03% to about 0.75%; about 0.03% to about 0.5%; about 0.03% to about 0.25%; about 0.03% to about 0.1%; about 0.03% to about 0.075%; about 0.03% to about 0.05%; and about 0.03%; all on a weight (mg)/volume (ml) basis, or on a weight/weight (mg) basis.

In another embodiment, the angiotensin peptide is administered in a polymer formulation, including but not limited to Poly-D. L-Lactic-Co-Glycolic Acid (PLGA), poly-lactic acid (PLA), PLA-PLGA co-polymers, polycaprolactone particles, and chitosan nanoparticles.

In all aspects of the invention, the angiotensin peptide, or salt thereof may be administered (or present in the pharmaceutical compositions) together with one or more (a) a lyoprotectant; (b) a surfactant; (c) a bulking agent; (d) a tonicity adjusting agent; (e) a stabilizer; (f) a preservative and/or (g) a buffer. In some embodiments, the buffer in the pharmaceutical composition is a Tris buffer, a histidine buffer, a phosphate buffer, a citrate buffer or an acetate buffer. The peptides may be administered with a lyoprotectant, e.g. sucrose, sorbitol or trehalose. In certain embodiments, the peptides may be administered with a preservative e.g. benzalkonium chloride, benzethonium, chlorohexidine, phenol m-cresol, benzyl alcohol, methylparaben, propylparaben, chlorobutanol, o-cresol, p-cresol, chlorocresol, phenylmercuric nitrate, thimerosal, benzoic acid, and various mixtures thereof. In other embodiments, the peptides may be administered with a bulking agent, like glycine. In yet other embodiments, the peptides may be administered with a surfactant e.g., polysorbate-20, polysorbate-40, polysorbate-60, polysorbate-65, polysorbate-80 polysorbate-85, poloxamer-188, sorbitan monolaurate, sorbitan monopalmitate, sorbitan monostearate, sorbitan monooleate, sorbitan trilaurate, sorbitan tristearate, sorbitan trioleaste, or a combination thereof. The peptides may be administered with a tonicity adjusting agent, e.g., a compound that renders the formulation substantially isotonic or isoosmotic with human blood. Exemplary tonicity adjusting agents include sucrose, sorbitol, glycine, methionine, mannitol, dextrose, inositol, sodium chloride, arginine and arginine hydrochloride. In other embodiments, the peptides may be administered with a stabilizer, e.g., a molecule which, when combined with the peptide substantially prevents or reduces chemical and/or physical instability of the protein of interest in lyophilized or liquid form. Exemplary stabilizers include sucrose, sorbitol, glycine, inositol, sodium chloride, methionine, arginine, and arginine hydrochloride, paraben, and combinations of methyl paraben and propyl paraben.

The angiotensin peptide may be the sole active agent in the pharmaceutical composition, or the composition may further comprise one or more other active agents suitable for the desired treatment. The methods may be used in conjunction with other therapies suitable for treating MS.

Examples

Multiple Sclerosis (MS) is a chronic autoimmune and neurodegenerative disease of the central nervous system (CNS) that is characterized by focal infiltration of leukocytes, including myelin-specific T cells, into the CNS, resulting destruction of myelin, demyelination, oxidative stress, axonal loss and ultimately, clinical symptoms and neurological disability. Experimental autoimmune encephalomyelitis (EAE) is a well-established animal model of MS that mimics many of the features of MS. We evaluated the ability of angiotensin peptide A(1-7) to modulate EAE disease course. For this study we used two common EAE models to study the efficacy of A(1-7), one that replicates the chronic progressive form of MS and the other that follows a relapsing-remitting course of the disease. Mice were immunized with peptides corresponding to major immunodominant regions of two myelin proteins: myelin oligodendrocyte protein 35-55 (MOG-EAE) immunization in C57BL6 mice to induce a chronic progressive disease, or proteolipid protein 139-151 (PLP-EAE) immunization in SJL/J mice induced a relapsing-remitting disease.

Immunization to Induce MOG-EAE 10 week old male C57BL/6 mice were immunized subcutaneously in 2 sites on their flank at 100 µl/site on day 0 with 200 µg MOG 35-55 peptide emulsified in IFA with 4 mg/ml *Mycobacterium tuberculosis* (M. tub) (CFA) (4-6 mice per group). Each mouse also received 2 intraperitoneal (i.p.) injections of *Bordatella pertussis* toxin (PTX) (250 ng in 100 µl) on the day of the first immunization and 2 days later (days 0 and 2). On day 7, mice received a booster inoculation with 200 µg MOG 35-55 emulsified in IFA only in a further 2 sites on their flank at 100 µl/site. At the time of immunization mice were anesthetized with Ketamine/Xylazine (80-100 mg/kg/IP/8-10 mg/kg/IP). Mice on the C57BL6 genetic background are relatively resistant to EAE, necessitating 2 immunizations with PTX to achieve disease in 90-100% mice.

MOG-EAE Disease Course

MOG-EAE in untreated mice shows a chronic progressive course in which an acute attack of neurological symptoms occurs approximately 9-12 days after immunization, where mice will develop clinical disease consisting of tail paralysis, ataxia, and hind limb and possibly forelimb paralysis. Mice will continue to accrue disability and will stabilize with a high level of disability at 18-20 days. MOG-EAE mimics the progressive forms of MS.

Immunization to Induce PLP-EAE

Female SJL/J mice, 10-weeks-old, were immunized subcutaneously in 4 sites on their flank (approximately 50 μl each) with 120 μg PLP-139-151 peptide emulsified in 200 μl CFA at baseline. Mice were anesthetized (as described for MOG-EAE) for the immunizations. SJL/J mice are highly susceptible to EAE induction by this method and require only one immunization to achieve disease in 90-100% of mice.

PLP-EAE Disease Course

PLP-EAE is a relapsing form of disease in which the first acute attack of neurological symptoms occurs at approximately 10-13 days after immunization, peaks between day 15 and 18, is followed by a period of recovery, or remission for about 10 days. 25-40 days after immunization ~75% of mice develop a second wave of paralysis (relapse). Relapses are often less severe and of shorter duration than the first attack. PLP-EAE mimics the relapsing-remitting form of MS.

Administration of A(1-7)

Mice were treated with (0.5, 1.0, 2.0 or 4.0 mg/kg/day) A(1-7) (or placebo (saline)), with administration being once daily (sc injection), twice daily (sc injection), or continuous (Alzet pump), following onset of clinical disease.

Assessment of Clinical Disease

In both EAE models, disease activity exhibits a typical pattern of symptoms, assessed daily as clinical scores, as follows: 0=no symptoms as compared with non-immunized mice, 0.5=weight loss and/or subtle weakness in tail or gripping of hindlimbs, 1=loss of muscle tone in tail and/or mild weakness in gripping of hindlimbs, 1.5=tail paralysis or very limp tail, hindlimbs have very weak grip, 2=hindlimb weakness, resulting in a "wobbly gait", or ataxia, 2.5=more severe ataxia and hindlimb weakness where mouse may drag one limb occasionally but can still move joints, 3=mild pareisis or paralysis of one (3.0) or both (3.5) hindlimbs and possible incontinence, 4=complete paralysis of both hindlimbs, 4.5=paresis or paralysis of forelimbs, 5=loss of temperature control and inactivity. Any mouse with a score of 4.5 or higher, or with >25% weight loss and/or a score of 4.0 accompanied by lack of interest in food or water, urinary incontinence and lack of grooming for more than 36 hours, is humanely euthanized. Supportive care, in the form of food (such as soft food pellets or peanut butter), water (given by hand twice daily) or cleaning of mice with urinary incontinence, is provided to mice as needed, however, the majority of mice remain active and are interested in eating, drinking, grooming and nest building.

A(1-7) Treatment in the Chronic Progressive MOG-EAE Model of MS

MOG-induced EAE is a severe MS disease model. Once disease is established treatment intervention can be limited. As a correlate, there are currently no FDA approved therapies specifically targeted for the treatment of progressive MS. A(1-7) treatment was started at day 10, when mice first demonstrated signs of clinical disease. Results suggest that once daily (FIG. 1A) or twice daily (FIG. 1B) treatment with 0.5 mg/kg A(1-7) results in a less severe disease course compared with control, non-treated, immunized mice up to 50 days post immunization.

A(1-7) Treatment in the Relapsing-Remitting PLP-EAE Model of MS

Current FDA approved therapies for the treatment of MS are for the relapsing-remitting form of the disease. Most treatments are immune modulators that decrease relapse rate and slow disease progression. However in most cases, over time, the patient still progresses. FIG. 1C provides data indicating that treatment with A(1-7) started 10 days after disease immunization, when the mice display the first clinical symptoms of disease, resulted in delayed onset of disease and that the disease was less severe compared to control non-treated immunized mice. Additionally the data indicate that A(1-7) treatment in PLP-EAE SJL mice improves disease course (less disability) with increasing duration of treatment.

Dose Response Findings of A(1-7) Treatment in the Chronic Progressive MOG-EAE Model of MS FIGS. 2 and 3 provide data demonstrating dose response findings of A(1-7) treatment, given either as twice daily injections (FIG. 2) or continuous delivery (FIG. 3), in the progressive MOG-EAE model and where A(1-7) treatment was started at day 11 at the first signs of clinical disease. FIG. 2 demonstrates that twice daily treatment with A(1-7) to give a total of 1.2 or 4 mg/kg/day is more effective in reducing clinical disease score than 0.5 mg/kg/day. All doses of A(1-7) given as twice daily injection improved clinical disease score compared to control saline treated mice. FIG. 3 demonstrates that treatment with 1 mg/kg/day continuous delivery A(1-7) is highly effective at inhibiting disease progression and maintaining reduced severity of the disease compared to control. Treatment with 2 mg/kg/day continuous delivery promotes restoration from disability compared to control saline treated mice (FIG. 3 and FIG. 4A).

A(1-7) Treatment in In Vitro Neurosphere Cultures.

Normal human progenitor cells were purchased from Clonetics (San Diego, Calif.) and cultured in Neural Progenitor Cell Maintenance Medium (NPMM) [Neural Progenitor Basal Medium containing human recombinant fibroblast growth factor-beta, human recombinant epidermal growth factor, neural survival factors, gentamycin and amphotericin B)]. The cells were thawed, diluted into NPMM and cultured for 24 hours in a 75 cm$^2$ flask. Until studies to assess differentiation, the cells were cultured in dedifferentiated spheroids. If the cells were cultured in suspension culture in the presence of A(1-7) for 4-7 days prior to placement of the cells on a culture substrate that allowed adherence and differentiation (as described further below), an increase in the number of cells able to undergo differentiation (proliferation) was observed.

In order to assess the differentiation of neuronal cells, the cells were seeded upon wells coated with 0.05% polyethyleneimine (PEI) substrate in borate buffer solution. The wells of a 96 well plate were coated with 0.05 ml of this solution overnight at room temperature. After the incubation, the substrate was removed by aspiration, rinsed with sterile water and allowed to dry before seeding of cells. Four days after plating, the number of cells undergoing differentiation, as assessed by neurite outgrowth) was counted The data are shown in FIG. 4, and demonstrate that A(1-7) treatment in vitro in neurosphere cell cultures promotes neurite outgrowth and proliferation with increasing doses of A(1-7) suggesting a direct neurorestorative effect of A(1-7).

We claim:

1. A method for limiting demyelination and/or promoting remyelination, comprising administering to a subject in need thereof an amount effective of a peptide comprising A(1-7), (Asp-Arg-Val-Tyr-Ile-His-Pro; (SEQ ID NO: 4), or salt thereof to limit demyelination and/or promote remyelination in the subject.

2. The method of claim 1, wherein the method is for limiting demyelination.

3. The method of claim 1, wherein the method is for promoting remyelination.

4. The method of claim 1, wherein the peptide is administered in a polymer formulation.

5. The method of claim 4, wherein the polymer formulation comprises a Poly-D,L-Lactic-Co-Glycolic Acid (PLGA) polymer, a poly-lactic acid (PLA), and co-polymers thereof, polycaprolactone particles, and chitosan nanoparticles.

6. The method of claim 4, wherein the method is for limiting demyelination.

7. The method of claim 4, wherein the method is for promoting remyelination.

8. The method of claim 5, wherein the method is for limiting demyelination.

9. The method of claim 5, wherein the method is for promoting remyelination.

* * * * *

SEQUENCE LISTING

```
<160> NUMBER OF SEQ ID NOS: 51

<210> SEQ ID NO 1
<211> LENGTH: 8
```

```
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is Asp, Glu, Asn, Acpc (1-aminocyclopentane
      carboxylic acid), Ala, Me2Gly, Pro, Bet, Glu(NH2), Gly, Asp(NH2)
      or is absent,
<220> FEATURE:
<221> NAME/KEY: MISC_FEATURE
<222> LOCATION: (1)..(1)
<223> OTHER INFORMATION: optional N-terminal H or Suc
<220> FEATURE:
<221> NAME/KEY: MISC_FEATURE
<222> LOCATION: (2)..(2)
<223> OTHER INFORMATION: Xaa is Arg, Lys, Ala, Orn, Ser(Ac), D-Arg or
      D-Lys,
<220> FEATURE:
<221> NAME/KEY: MISC_FEATURE
<222> LOCATION: (2)..(2)
<223> OTHER INFORMATION: optional N-terminal Cit or Sar
<220> FEATURE:
<221> NAME/KEY: MISC_FEATURE
<222> LOCATION: (3)..(3)
<223> OTHER INFORMATION: Xaa is Val, Ala, Leu, norLeu, Ile, Gly, Lys,
      Pro, Acpc or Tyr
<220> FEATURE:
<221> NAME/KEY: MISC_FEATURE
<222> LOCATION: (3)..(3)
<223> OTHER INFORMATION: optional N-terminal Aib
<220> FEATURE:
<221> NAME/KEY: MISC_FEATURE
<222> LOCATION: (4)..(4)
<223> OTHER INFORMATION: Xaa is Tyr, Tyr(PO3)2, Thr, Ser, homoSer,
      azaTyr, or Ala
<220> FEATURE:
<221> NAME/KEY: MISC_FEATURE
<222> LOCATION: (5)..(5)
<223> OTHER INFORMATION: Xaa is Ile, Ala, Leu, norLeu, Val or Gly
<220> FEATURE:
<221> NAME/KEY: MISC_FEATURE
<222> LOCATION: (6)..(6)
<223> OTHER INFORMATION: Xaa is His, Arg or 6-NH2-Phe
<220> FEATURE:
<221> NAME/KEY: MISC_FEATURE
<222> LOCATION: (7)..(7)
<223> OTHER INFORMATION: Xaa is Pro or Ala
<220> FEATURE:
<221> NAME/KEY: MISC_FEATURE
<222> LOCATION: (8)..(8)
<223> OTHER INFORMATION: Xaa is Phe, Phe(Br), Ile or Tyr, excluding
      sequences including R4 as a terminal Tyr group.

<400> SEQUENCE: 1

Xaa Xaa Xaa Xaa Xaa Xaa Xaa Xaa
1               5

<210> SEQ ID NO 2
<211> LENGTH: 7
<212> TYPE: PRT
<213> ORGANISM: Artificial Sequence
<220> FEATURE:
<223> OTHER INFORMATION: Synthetic

<400> SEQUENCE: 2

Arg Val Tyr Ile His Pro Phe
1               5

<210> SEQ ID NO 3
<211> LENGTH: 6
<212> TYPE: PRT
<213> ORGANISM: Artificial Sequence
<220> FEATURE:
```

```
<223> OTHER INFORMATION: Synthetic

<400> SEQUENCE: 3

Val Tyr Ile His Pro Phe
1               5

<210> SEQ ID NO 4
<211> LENGTH: 7
<212> TYPE: PRT
<213> ORGANISM: Artificial Sequence
<220> FEATURE:
<223> OTHER INFORMATION: Synthetic

<400> SEQUENCE: 4

Asp Arg Val Tyr Ile His Pro
1               5

<210> SEQ ID NO 5
<211> LENGTH: 6
<212> TYPE: PRT
<213> ORGANISM: Artificial Sequence
<220> FEATURE:
<223> OTHER INFORMATION: Synthetic

<400> SEQUENCE: 5

Arg Val Tyr Ile His Pro
1               5

<210> SEQ ID NO 6
<211> LENGTH: 5
<212> TYPE: PRT
<213> ORGANISM: Artificial Sequence
<220> FEATURE:
<223> OTHER INFORMATION: Synthetic

<400> SEQUENCE: 6

Val Tyr Ile His Pro
1               5

<210> SEQ ID NO 7
<211> LENGTH: 4
<212> TYPE: PRT
<213> ORGANISM: Artificial Sequence
<220> FEATURE:
<223> OTHER INFORMATION: Synthetic

<400> SEQUENCE: 7

Ile His Pro Phe
1

<210> SEQ ID NO 8
<211> LENGTH: 6
<212> TYPE: PRT
<213> ORGANISM: Artificial Sequence
<220> FEATURE:
<223> OTHER INFORMATION: Synthetic

<400> SEQUENCE: 8

Asp Arg Val Tyr Ile His
1               5

<210> SEQ ID NO 9
<211> LENGTH: 5
<212> TYPE: PRT
<213> ORGANISM: Artificial Sequence
<220> FEATURE:
<223> OTHER INFORMATION: Synthetic
```

```
<400> SEQUENCE: 9

Asp Arg Val Tyr Ile
1               5

<210> SEQ ID NO 10
<211> LENGTH: 4
<212> TYPE: PRT
<213> ORGANISM: Artificial Sequence
<220> FEATURE:
<223> OTHER INFORMATION: Synthetic

<400> SEQUENCE: 10

Asp Arg Val Tyr
1

<210> SEQ ID NO 11
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Nle

<400> SEQUENCE: 11

Arg Leu Tyr Ile His Pro Phe
1               5

<210> SEQ ID NO 12
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (4)..(4)
<223> OTHER INFORMATION: Nle

<400> SEQUENCE: 12

Arg Val Tyr Leu His Pro Phe
1               5

<210> SEQ ID NO 13
<211> LENGTH: 8
<212> TYPE: PRT
<213> ORGANISM: Artificial Sequence
<220> FEATURE:
<223> OTHER INFORMATION: Synthetic

<400> SEQUENCE: 13

Asp Arg Pro Tyr Ile His Pro Phe
1               5

<210> SEQ ID NO 14
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (3)..(3)
<223> OTHER INFORMATION: Nle

<400> SEQUENCE: 14
```

Asp Arg Leu Tyr Ile His Pro
1               5

<210> SEQ ID NO 15
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is Asp or Glu or is absent
<220> FEATURE:
<221> NAME/KEY: MISC_FEATURE
<222> LOCATION: (2)..(2)
<223> OTHER INFORMATION: Xaa is Arg, Lys, or Ala
<220> FEATURE:
<221> NAME/KEY: MISC_FEATURE
<222> LOCATION: (3)..(3)
<223> OTHER INFORMATION: Xaa is Val, Ala, Leu, norLeu, Ile, Gly, Lys, or
      Pro
<220> FEATURE:
<221> NAME/KEY: MISC_FEATURE
<222> LOCATION: (4)..(4)
<223> OTHER INFORMATION: Xaa is Tyr or homoSer
<220> FEATURE:
<221> NAME/KEY: MISC_FEATURE
<222> LOCATION: (5)..(5)
<223> OTHER INFORMATION: Xaa is Ile, Ala, Leu, norLeu, Val or Gly
<220> FEATURE:
<221> NAME/KEY: MISC_FEATURE
<222> LOCATION: (6)..(6)
<223> OTHER INFORMATION: Xaa is His or Arg
<220> FEATURE:
<221> NAME/KEY: MISC_FEATURE
<222> LOCATION: (7)..(7)
<223> OTHER INFORMATION: Xaa is Pro or Ala
<220> FEATURE:
<221> NAME/KEY: MISC_FEATURE
<222> LOCATION: (8)..(8)
<223> OTHER INFORMATION: Xaa is Phe, Ile or is absent

<400> SEQUENCE: 15

Xaa Xaa Xaa Xaa Xaa Xaa Xaa Xaa
1               5

<210> SEQ ID NO 16
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (3)..(3)
<223> OTHER INFORMATION: Nle

<400> SEQUENCE: 16

Asp Arg Leu Tyr Ile
1               5

<210> SEQ ID NO 17
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (3)..(3)
<223> OTHER INFORMATION: Nle

```
<400> SEQUENCE: 17

Asp Arg Leu Tyr Ile His
1               5

<210> SEQ ID NO 18
<211> LENGTH: 8
<212> TYPE: PRT
<213> ORGANISM: Artificial Sequence
<220> FEATURE:
<223> OTHER INFORMATION: Synthetic

<400> SEQUENCE: 18

Asp Arg Val Tyr Val His Pro Phe
1               5

<210> SEQ ID NO 19
<211> LENGTH: 8
<212> TYPE: PRT
<213> ORGANISM: Artificial Sequence
<220> FEATURE:
<223> OTHER INFORMATION: Synthetic

<400> SEQUENCE: 19

Asn Arg Val Tyr Val His Pro Phe
1               5

<210> SEQ ID NO 20
<211> LENGTH: 11
<212> TYPE: PRT
<213> ORGANISM: Artificial Sequence
<220> FEATURE:
<223> OTHER INFORMATION: Synthetic

<400> SEQUENCE: 20

Ala Pro Gly Asp Arg Ile Tyr Val His Pro Phe
1               5                   10

<210> SEQ ID NO 21
<211> LENGTH: 8
<212> TYPE: PRT
<213> ORGANISM: Artificial Sequence
<220> FEATURE:
<223> OTHER INFORMATION: Synthetic

<400> SEQUENCE: 21

Glu Arg Val Tyr Ile His Pro Phe
1               5

<210> SEQ ID NO 22
<211> LENGTH: 8
<212> TYPE: PRT
<213> ORGANISM: Artificial Sequence
<220> FEATURE:
<223> OTHER INFORMATION: Synthetic

<400> SEQUENCE: 22

Asp Lys Val Tyr Ile His Pro Phe
1               5

<210> SEQ ID NO 23
<211> LENGTH: 8
<212> TYPE: PRT
<213> ORGANISM: Artificial Sequence
<220> FEATURE:
<223> OTHER INFORMATION: Synthetic

<400> SEQUENCE: 23
```

Asp Arg Ala Tyr Ile His Pro Phe
1               5

<210> SEQ ID NO 24
<211> LENGTH: 8
<212> TYPE: PRT
<213> ORGANISM: Artificial Sequence
<220> FEATURE:
<223> OTHER INFORMATION: Synthetic

<400> SEQUENCE: 24

Asp Arg Val Thr Ile His Pro Phe
1               5

<210> SEQ ID NO 25
<211> LENGTH: 8
<212> TYPE: PRT
<213> ORGANISM: Artificial Sequence
<220> FEATURE:
<223> OTHER INFORMATION: Synthetic

<400> SEQUENCE: 25

Asp Arg Val Tyr Leu His Pro Phe
1               5

<210> SEQ ID NO 26
<211> LENGTH: 8
<212> TYPE: PRT
<213> ORGANISM: Artificial Sequence
<220> FEATURE:
<223> OTHER INFORMATION: Synthetic

<400> SEQUENCE: 26

Asp Arg Val Tyr Ile Arg Pro Phe
1               5

<210> SEQ ID NO 27
<211> LENGTH: 8
<212> TYPE: PRT
<213> ORGANISM: Artificial Sequence
<220> FEATURE:
<223> OTHER INFORMATION: Synthetic

<400> SEQUENCE: 27

Asp Arg Val Tyr Ile His Ala Phe
1               5

<210> SEQ ID NO 28
<211> LENGTH: 8
<212> TYPE: PRT
<213> ORGANISM: Artificial Sequence
<220> FEATURE:
<223> OTHER INFORMATION: Synthetic

<400> SEQUENCE: 28

Asp Arg Val Tyr Ile His Pro Tyr
1               5

<210> SEQ ID NO 29
<211> LENGTH: 8
<212> TYPE: PRT
<213> ORGANISM: Artificial Sequence
<220> FEATURE:
<223> OTHER INFORMATION: Synthetic

<400> SEQUENCE: 29

```
Pro Arg Val Tyr Ile His Pro Phe
1               5

<210> SEQ ID NO 30
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (4)..(4)
<223> OTHER INFORMATION: PHOSPHORYLATION

<400> SEQUENCE: 30

Asp Arg Val Tyr Ile His Pro Phe
1               5

<210> SEQ ID NO 31
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (3)..(3)
<223> OTHER INFORMATION: Nle

<400> SEQUENCE: 31

Asp Arg Leu Tyr Ile His Pro Phe
1               5

<210> SEQ ID NO 32
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (5)..(5)
<223> OTHER INFORMATION: Nle

<400> SEQUENCE: 32

Asp Arg Val Tyr Leu His Pro Phe
1               5

<210> SEQ ID NO 33
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: homoSer

<400> SEQUENCE: 33

Asp Arg Val Xaa Tyr Ile His Pro Phe
1               5

<210> SEQ ID NO 34
<211> LENGTH: 7
<212> TYPE: PRT
<213> ORGANISM: Artificial Sequence
<220> FEATURE:
<223> OTHER INFORMATION: Synthetic
<220> FEATURE:
```

```
<221> NAME/KEY: MISC_FEATURE
<222> LOCATION: (1)..(1)
<223> OTHER INFORMATION: optional N-terminal H, Citron or Sar
<220> FEATURE:
<221> NAME/KEY: MISC_FEATURE
<222> LOCATION: (1)..(1)
<223> OTHER INFORMATION: Xaa is Arg, Lys, Ala, Orn, Ser(Ac), D-Arg or
      D-Lys;
<220> FEATURE:
<221> NAME/KEY: MISC_FEATURE
<222> LOCATION: (2)..(2)
<223> OTHER INFORMATION: Xaa is Val, Ala, Leu, norLeu, Ile, Gly, Lys,
      Pro, Acpc or Tyr
<220> FEATURE:
<221> NAME/KEY: MISC_FEATURE
<222> LOCATION: (2)..(2)
<223> OTHER INFORMATION: optional N-terminal Aib
<220> FEATURE:
<221> NAME/KEY: MISC_FEATURE
<222> LOCATION: (3)..(3)
<223> OTHER INFORMATION: Xaa is Tyr, Tyr(PO3)2, Thr, Ser, homoSer,
      azaTyr, or Ala
<220> FEATURE:
<221> NAME/KEY: MISC_FEATURE
<222> LOCATION: (4)..(4)
<223> OTHER INFORMATION: Xaa is Ile, Ala, Leu, norLeu, Val or Gly
<220> FEATURE:
<221> NAME/KEY: MISC_FEATURE
<222> LOCATION: (5)..(5)
<223> OTHER INFORMATION: Xaa is His, Arg or 6-NH2-Phe
<220> FEATURE:
<221> NAME/KEY: MISC_FEATURE
<222> LOCATION: (6)..(6)
<223> OTHER INFORMATION: Xaa is Pro or Ala
<220> FEATURE:
<221> NAME/KEY: MISC_FEATURE
<222> LOCATION: (7)..(7)
<223> OTHER INFORMATION: Xaa is Phe, Phe(Br), Ile or Tyr, excluding
      sequences including R4 as a terminal Tyr group.

<400> SEQUENCE: 34

Xaa Xaa Xaa Xaa Xaa Xaa Xaa
1               5

<210> SEQ ID NO 35
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optional N-terminal H, Citron, or Sar
<220> FEATURE:
<221> NAME/KEY: MISC_FEATURE
<222> LOCATION: (1)..(1)
<223> OTHER INFORMATION: Xaa is Arg, Lys, Ala, Orn, Ser(Ac), D-Arg or
      D-Lys;
<220> FEATURE:
<221> NAME/KEY: MISC_FEATURE
<222> LOCATION: (2)..(2)
<223> OTHER INFORMATION: Xaa is Val, Ala, Leu, norLeu, Ile, Gly, Lys,
      Pro, Acpc or Tyr;
<220> FEATURE:
<221> NAME/KEY: MISC_FEATURE
<222> LOCATION: (2)..(2)
<223> OTHER INFORMATION: optional N-terminal Aib
<220> FEATURE:
<221> NAME/KEY: MISC_FEATURE
<222> LOCATION: (4)..(4)
<223> OTHER INFORMATION: Xaa is Ile, Ala, Leu, norLeu, Val or Gly

<400> SEQUENCE: 35

Xaa Xaa Tyr Xaa His Pro Phe
1               5
```

```
<210> SEQ ID NO 36
<211> LENGTH: 7
<212> TYPE: PRT
<213> ORGANISM: Artificial Sequence
<220> FEATURE:
<223> OTHER INFORMATION: Synthetic

<400> SEQUENCE: 36

Arg Val Tyr Gly His Pro Phe
1               5

<210> SEQ ID NO 37
<211> LENGTH: 7
<212> TYPE: PRT
<213> ORGANISM: Artificial Sequence
<220> FEATURE:
<223> OTHER INFORMATION: Synthetic

<400> SEQUENCE: 37

Arg Val Tyr Ala His Pro Phe
1               5

<210> SEQ ID NO 38
<211> LENGTH: 7
<212> TYPE: PRT
<213> ORGANISM: Artificial Sequence
<220> FEATURE:
<223> OTHER INFORMATION: Synthetic

<400> SEQUENCE: 38

Asp Arg Val Ala Ile His Pro
1               5

<210> SEQ ID NO 39
<211> LENGTH: 7
<212> TYPE: PRT
<213> ORGANISM: Artificial Sequence
<220> FEATURE:
<223> OTHER INFORMATION: Synthetic

<400> SEQUENCE: 39

Asp Arg Pro Tyr Ile His Pro
1               5

<210> SEQ ID NO 40
<211> LENGTH: 7
<212> TYPE: PRT
<213> ORGANISM: Artificial Sequence
<220> FEATURE:
<223> OTHER INFORMATION: Synthetic

<400> SEQUENCE: 40

Asp Arg Lys Tyr Ile His Pro
1               5

<210> SEQ ID NO 41
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (3)..(3)
<223> OTHER INFORMATION: Nle

<400> SEQUENCE: 41
```

```
Asp Arg Tyr Ile His Pro
1               5
```

<210> SEQ ID NO 42
<211> LENGTH: 8
<212> TYPE: PRT
<213> ORGANISM: Artificial Sequence
<220> FEATURE:
<223> OTHER INFORMATION: Synthetic

<400> SEQUENCE: 42

```
Asp Arg Val Tyr Ile His Pro Ile
1               5
```

<210> SEQ ID NO 43
<211> LENGTH: 7
<212> TYPE: PRT
<213> ORGANISM: Artificial Sequence
<220> FEATURE:
<223> OTHER INFORMATION: Synthetic

<400> SEQUENCE: 43

```
Arg Val Ala Ile His Pro Phe
1               5
```

<210> SEQ ID NO 44
<211> LENGTH: 7
<212> TYPE: PRT
<213> ORGANISM: Artificial Sequence
<220> FEATURE:
<223> OTHER INFORMATION: Synthetic

<400> SEQUENCE: 44

```
Arg Val Ala Ile His Pro Phe
1               5
```

<210> SEQ ID NO 45
<211> LENGTH: 8
<212> TYPE: PRT
<213> ORGANISM: Artificial Sequence
<220> FEATURE:
<223> OTHER INFORMATION: Synthetic

<400> SEQUENCE: 45

```
Gly Arg Val Tyr Ile His Pro Phe
1               5
```

<210> SEQ ID NO 46
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (4)..(4)
<223> OTHER INFORMATION: Nle

<400> SEQUENCE: 46

```
Arg Val Tyr Leu His Pro Phe
1               5
```

<210> SEQ ID NO 47
<211> LENGTH: 8
<212> TYPE: PRT
<213> ORGANISM: Artificial Sequence
<220> FEATURE:

```
<223> OTHER INFORMATION: Synthetic
<220> FEATURE:
<221> NAME/KEY: MOD_RES
<222> LOCATION: (3)..(3)
<223> OTHER INFORMATION: Acp

<400> SEQUENCE: 47

Asp Arg Xaa Tyr Ile His Pro Phe
1               5

<210> SEQ ID NO 48
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Orn

<400> SEQUENCE: 48

Asp Xaa Val Tyr Ile His Pro Phe
1               5

<210> SEQ ID NO 49
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: C-terminal Citron

<400> SEQUENCE: 49

Asp Val Tyr Ile His Pro Phe
1               5

<210> SEQ ID NO 50
<211> LENGTH: 7
<212> TYPE: PRT
<213> ORGANISM: Artificial Sequence
<220> FEATURE:
<223> OTHER INFORMATION: Synthetic

<400> SEQUENCE: 50

Asp Arg Pro Ala Ile His Pro
1               5

<210> SEQ ID NO 51
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (3)..(3)
<223> OTHER INFORMATION: 3Hyp

<400> SEQUENCE: 51

Asp Arg Pro Ala Ile His Pro
1               5
```